United States Patent [19]

D'Silva et al.

[11] 4,339,444
[45] Jul. 13, 1982

[54] NOVEL OXIME-PHOSPHATE COMPOUNDS

[75] Inventors: Themistocles D. J. D'Silva, South Charleston; Leonard E. Hodakowski, St. Albans, both of W. Va.

[73] Assignee: Union Carbide Corporation, Danbury, Conn.

[21] Appl. No.: 249,819

[22] Filed: Apr. 1, 1981

[51] Int. Cl.$^3$ .................... A01N 57/12; A01N 57/14; A01N 57/16; C07F 9/09
[52] U.S. Cl. ................................ 424/202; 260/453.8; 260/944; 424/200; 424/211; 544/3; 544/53; 544/57; 548/119; 549/5; 549/7; 549/8
[58] Field of Search ................ 260/453.8, 944; 544/3, 544/53, 57; 548/119; 549/5, 7, 8; 424/200, 202, 211

[56] References Cited

U.S. PATENT DOCUMENTS

| | | | |
|---|---|---|---|
| 2,957,016 | 10/1960 | Diamond | 260/461 |
| 3,281,430 | 10/1966 | Addor | 549/7 X |
| 3,632,758 | 1/1972 | Partos et al. | 424/211 |
| 3,660,541 | 5/1972 | Gutman | 260/944 X |
| 3,717,690 | 2/1973 | Newman | 260/945 |
| 3,897,516 | 7/1975 | Gutman | 260/944 X |
| 3,949,023 | 4/1976 | Sasaki et al. | 260/944 |

*Primary Examiner*—Richard Raymond
*Attorney, Agent, or Firm*—Andrea L. Loshin; John A. Shedden; Robert C. Brown

[57] ABSTRACT

Novel acyclic and heterocyclic oxime phosphate compounds have been found to exhibit insecticidal, miticidal and nematocidal activity.

52 Claims, No Drawings

NOVEL OXIME-PHOSPHATE COMPOUNDS

This invention relates to novel insecticidal, acaricidal and nematocidal oxime phosphate compounds. This invention also relates to pesticidal compositions for controlling insects and mites, as well as to methods of controlling insects and mites by subjecting them to an insecticidally, miticidally or nematocidally effective amount of a compound of this invention.

The novel compounds of this invention are compounds of the formula:

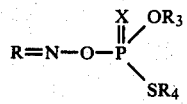

wherein: X is oxygen or sulfur; $R_3$ and $R_4$ are individually alkyl; provided that the total number of carbon atoms in each of $R_3$ and $R_4$ does not exceed six; R is:

   1.

wherein: $R_1$ is alkyl, cycloalkyl or phenyl, all of which may be unsubstituted or substituted with one or more alkyl, halogen, alkoxy or alkylthio substituents; provided that the total number of aliphatic carbon atoms in any alkyl, alkoxy or alkylthio substituent may not exceed eight; and provided further that the total number of aliphatic carbon atoms in $R_1$ may not exceed sixteen; and provided further that when $R_1$ is cycloalkyl, the total number of aliphatic carbon atoms in the cycloalkyl ring structure may be no less than three and may not exceed six; $R_2$ is alkyl, provided that the total number of aliphatic carbon atoms in $R_2$ does not exceed eight; or

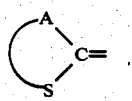   2.

wherein: A is a three- or four-membered divalent aliphatic chain, which may be optionally substituted by one or more alkyl or acyl groups each containing no more than six carbon atoms, and which may include in said chain one or more divalent: sulfur, sulfinyl, sulfonyl, oxygen, carbonyl, thiono or dicyanomethylidene moieties, or amino moieties, which may be optionally substituted with alkyl, alkenyl, alkoxyalkyl, or acyl groups having no more than six carbon atoms, or imino moieties of the formula:

wherein Y is alkyl, alkenyl, alkynyl, dialkylamino, cyano, alkylsulfonyl, aryl or arylsulfonyl groups, said aryl groups being optionally substituted with halogen or alkyl substituents having no more than ten carbon atoms.

Generally, the preferred compounds of this invention are those wherein: $R_3$ and $R_4$ are different alkyl moieties; $R_3$ is ethyl and $R_4$ is n-propyl.

Also preferred are those compounds wherein X is oxygen.

Also preferred are compounds wherein R is a group of the formula:

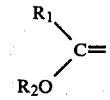

wherein $R_1$ is alkyl and $R_2$ is methyl or ethyl; or $R_1$ is phenyl and $R_2$ is methyl or ethyl.

Additional preferred compounds are those wherein R is a group of the formula:

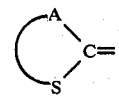

wherein A, C and S form a 2-oximino-1,4-dithiane; 2-oximino-1,3-dithiane; 4-oximino-1,3-dithiolane; 2-oximino-tetrahydro-1,4-thiazine-3-one; 2-oximino-1,3-dithiolane; 2-dicyanomethylidene-4-oximino-1,3-dithiolane; 2-oximinothiophane; 4-oximino-1,3-oxathiolane; 5-oximino-1,3-thiazolidin-4-one, 2-oximino-1,3-thiazolidin-4-one; 2-oximino-tetrahydro-1,4-thiazine; 2-oximino-4-thiono-1,3-thiazolidine; 2-oximino-tetrahydro-1,4-thiazin-5-one ring structure, wherein said 2-oximino-tetrahydro-1,4-thiazine ring may be substituted by an acyl substituent on its nitrogen moiety.

Activity is particularly great in compounds wherein R is a 2-imino-4-oximino-1,3-dithiolane ring structure substituted with alkyl or dialkylamino moieties or wherein R is a 2-oximino-1,3-thiazolidin-4-one ring structure substituted with alkyl, alkoxyalkyl, or alkenyl moieties.

The novel oxime phosphate compounds of this invention can be conveniently prepared by three general methods. The first method is illustrated by the general reaction method set forth below:

METHOD I

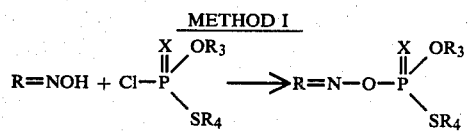

Method I is a one-step reaction wherein an appropriate oxime is reacted with a stoichiometric amount of an appropriate chlorophosphate compound in the presence of at least a stoichiometric amount of an acid acceptor and an inert solvent.

Methods II and III, illustrated by the general reaction methods below, are two-step methods wherein an appropriate oxime is reacted with an appropriate dihalophosphorus compound in the presence of a stoichiometric amount or slight excess of an acid acceptor and an inert solvent.

METHOD II

STEP A

-continued

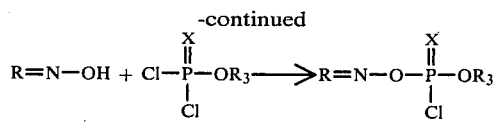

STEP B

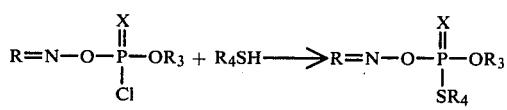

METHOD III
STEP A

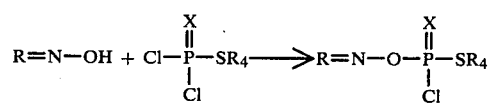

STEP B

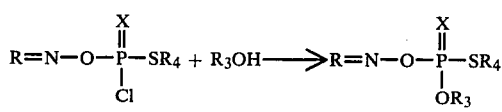

The reactions illustrated above in Methods I, II and III are conducted in the presence of an acid acceptor which can be either an organic or inorganic base. Illustrative of organic bases which may be used are tertiary amines such as trimethyl amine, triethyl amine, pyridine, 4-dimethylamino pyridine, 1,4-diazabicyclo [2.2.2.] octane. Examples of inorganic bases which may be used are sodium carbonate, potassium carbonate, sodium hydroxide, sodium hydride and the like.

When an inorganic base is used phase transfer agents may be used to facilitate the transfer of the base across the organic/inorganic phase interface. Illustrative of useful phase transfer agents are crown ether compounds, quaternary ammonium halide compounds and the like.

It is preferable to conduct the reactions in the presence of an inert solvent. In general, most organic solvents that are inert to the reactants or reaction conditions may be employed. Illustrative of suitable solvents are aromatic hydrocarbons such as toluene, xylene, naphthalene, and the like; aliphatic hydrocarbons such as methylene chloride, chloroform, carbon tetrachloride and mono-, di- and trichloro ethylene; low-boiling aliphatic ketones and nitriles such as acetone, methylethyl ketone, methylisopropyl ketone, methylisobutyl ketone, acetonitrile, and propionitrile; and ethers such as diethylether, dioxane and tetrahydrofuran. Solvents which are most preferred are acetone, acetonitrile and methylene chloride.

The reactions may also be conducted in the presence of an excess of an acid acceptor which also functions as the solvent. Illustrative of such multi-functional solvents are N,N-dimethyl aniline, pyridine, α-picoline, and any lutidine, collidine or any like aromatic or heterocyclic tertiary amine compound.

The reactions may be conducted over a wide range of temperatures and pressures. It is preferable to conduct them at a temperature between −40° C. and 120° C. and at atmospheric or autogeneous pressure.

The phosphorus halides and dihalides used as reactants in the above methods are known materials which can be obtained commercially or prepared in accordance with conventional methods known to those skilled in the art.

The alicyclic oxime precursors of the formula:

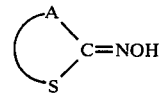

used in the preparation of the novel oxime phosphate compounds of this invention can be prepared by a variety of methods.

The oximino-thiazin-5-one compounds used as starting materials in preparing the compounds of this invention can be prepared by the methods disclosed in U.S. Pat. No. 4,071,627. In one method, a solution of α-aminoisobutyraldoxime and water is stirred and cooled to 0° C. Chlorine is added to the solution and the mixture is stirred. Ethyl mercaptoacetate and a base, such as sodium hydroxide, are added to produce an oximino-tetrahydro-1,4-thiazin-5-one.

The oximino-thiazin-3-one compounds can be prepared in accordance with a method disclosed in U.S. Pat. No. 3,894,150. Ethoxycarbonylformhydroxamoyl chloride is added to a solution of sodium hydroxide, ethanol and aminoethanethiol to produce an oximino-tetrahydro-1,4-thiazin-3-one.

The thiazolidinone oxime compounds used as starting materials in Methods I, II and III can be prepared in accordance with the methods described in U.S. Pat. No. 3,767,662. A mixture of acetone, thioglycolic acid and methylammonium carbonate in benzene is heated to produce a thiazolidinone ring. To this is added sodium hydride in anhydrous benzene and isopropyl nitrite yielding an oximino-thiazolidinone.

The oximino dithiolane ring structures used as starting materials in preparing the compounds of this invention can be prepared by one of the methods disclosed in U.S. Pat. No. 4,156,731. An appropriately-substituted dithiolate compound is reacted with either an appropriate 2-chlorohydroxamoyl chloride compound or nitro-substituted carbamate compound to produce the oximino-dithiolane.

The oximino-oxathiolane and oximino-oxathiane ring compounds can be prepared in accordance with the methods disclosed in U.S. Pat. No. 3,956,500. To prepare oxathiolane oxime compounds, nitroethanol is combined with hydrochloric acid, paraformaldehyde and calcium chloride. After cooling and distilling, the mixture is combined with thiolacetic acid. The product of this reaction is reacted with sodium hydroxide to produce oximino-oxathiolane. Oxathiane oximes can be prepared by reacting bis-2-bromoethyl ether with sodium nitrite and dimethylsulfoxide. The product of this reaction, bromoethyloxy-nitroethane is then combined with potassium thioacetate. By adding ethanolic sodium hydroxide and 2-(2-acetylthioethoxy)-1-nitroethane to the product, one skilled in the art can obtain the desired cyclic oximino-oxathiane.

The following examples are illustrative of the methods of preparing the novel compounds of this invention:

EXAMPLE I

Preparation of O-Ethyl-S-n-propyl-O-(5,5-dimethyl-2-methylimino-1,3-dithiolane-4-ylimino)-phosphorothioate (Method I)

A 100 ml flask was equipped with a magnetic stirrer, condenser, drying tube and thermometer. The glassware was dried thoroughly and charged with 3.6 g (0.019 mole) of 5,5-dimethyl-2-methylimino-1,3-dithiolane-4-oxime, 25 ml acetone and 3 g (0.021 mole) potassium carbonate. The mixture was heated to 50° C. for thirty minutes and then cooled to 40° C. at which time 3.44 g (0.017 mole) of O-ethyl-S-propyl phosphorochloridate was added dropwise. The material was then allowed to stir overnight at room temperature.

The material was poured into 150 ml of water and extracted with toluene (2×100 ml). The toluene layer was extracted with water (2×100 ml) and then with 2 N sodium hydroxide and again with water until the pH was 7. The toluene solution was dried with anhydrous magnesium sulfate and filtered through carbon black. The resulting solution was concentrated and purified on a low pressure liquid chromatography column to yield 3.0 g of a viscous oil as the desired product.

Calc'd for $C_{11}H_{21}N_2O_3PS_3$: C, 37.08; H, 5.90. Found: C, 36.82; H, 6.04.

EXAMPLE II

Preparation of O-Ethyl-S-propyl-O-(3-allyl-5,5-dimethyl-4-oxo-1,3-thiazolidin-2-ylimino)-phosphorothioate (Method I)

A 100 ml flask was equipped with a magnetic stirrer, condenser, drying tube and thermometer. The glassware was dried thoroughly and charged with 4.0 g (0.02 mole) of 3-allyl-5,5-dimethyl-4-oxo-thiazolidine-2-oxime, 50 ml acetone, and 3.17 g (0.023 mole) potassium carbonate. The mixture was heated to 50° C. for thirty minutes and then cooled to 40° at which time 4.5 g (0.022 mole) of O-ethyl-S-n-propyl phosphorochloridate was added dropwise. The material was then allowed to stir overnight at room temperature.

The mixture was extracted with ethyl ether and toluene and the organic layers combined and washed with sodium bicarbonate until the pH 7. The organic layer was dried with anhydrous magnesium sulfate, filtered and concentrated. The residue was dissolved in pentane and cooled to −70° C. at which time the pentane layer separated from an oil. The pentane was decanted and the oil taken up in ethyl ether, dried, filtered and concentrated to yield 1.0 g of the desired product.

Calc'd for $C_{13}H_{23}N_2O_4PS_2$: C, 42.62; H, 6.28. Found: C, 42.45; H, 6.50.

EXAMPLE III

Preparation of O-Ethyl-S-propyl-O-(5-methyl-1,3-oxathiolan-4-ylimino)-phosphorothioate (Method I)

A 100 ml flask was equipped with a magnetic stirrer, condenser, drying tube and thermometer. The glassware was thoroughly dried and charged with 5.32 g (0.04 mole) of 5-methyl-4-oximino-1,3-oxathiolane, 50 ml acetonitrile and 6.38 (0.046 mole) potassium carbonate. The mixture was heated to 55° C. for one hour and then cooled to 40° C. at which time 8.10 g (0.04 mole) of O-ethyl-S-n-propyl phosphorochloridate was added dropwise. The material was then heated for an additional six hours at 55° C. and then cooled to room temperature and stirred overnight.

The material was poured into 150 ml of water and extracted with ethyl ether (1×100 ml), toluene (1×100 ml) and methylene chloride (1×50 ml). The organic layers were combined and washed quickly with 200 ml 8 N sodium hydroxide followed by several water washes. The organic layer was dried over magnesium sulfate (anhydrous), containing carbon black, and then filtered and concentrated. The resulting oil was purified on a low pressure liquid chromatography unit to yield 1.2 g of the desired product.

Calc'd for $C_9H_{18}NO_4PS_2$: C, 36.12; H, 6.02. Found: C, 36.54; H, 6.11.

EXAMPLE IV

Preparation of Acetohydroxamic acid methyl ester (Method I, Preparation of oxamic acid ester reactant)

A 170 g (1.23 mol) quantity of anhydrous potassium carbonate was dissolved in 375 ml of distilled water and cooled with an ice bath to 5° C. To this solution was added 67.2 g (0.61 mol) of methylacetimidate hydrochloride. The ice bath was removed and the reaction mixture was warmed to 25° C. over a ten-minute period and then stirred for an additional ten minutes. The aqueous solution was extracted with ether and the combined ether layers were extracted with water. The resulting ether solution was added to a vigorously stirred solution of 52.9 g (0.76 mol) of hydroxylamine hydrochloride in 180 ml of water which had been cooled to 5° C. The reactants were stirred at 25° C. for ten minutes. The ether layer was separated and the aqueous layer was extracted with ether. The combined ether layers were dried with sodium sulfate and concentrated under vacuum to give 13.1 g (24%) of acetohydroxamic acid methyl ester.

EXAMPLE V

Preparation of Cyclohexanehydroxamic acid methyl ester (Method I, Preparation of oxamic acid ester reactant)

A 17.10 g (0.13 mol) quantity of cyclohexanecarboxaldehyde oxime and sodium bicarbonate in an aqueous methanol reaction medium, were dissolved in 250 ml of ether and cooled in an ice bath. Into this medium was bubbled 9.55 g (0.13 mol) of chlorine gas at a rate of 0.7 g per minute. The reaction mixture was allowed to stand at 25° C. for 20 minutes before filtering. Concentration of the filtrate afforded 16.7 g of cyclohexanehydroxamoyl chloride. An 8.0 g (49.5 mmol) quantity of cyclohexanehydroxamoyl chloride was dissolved in 125 ml of methanol and slowly added over 5 hours to a freshly prepared solution of sodium methoxide (4.6 g, i.e. 200 mmol of sodium in 250 ml of methanol). The reaction mixture was stirred overnight at 25° C., concentrated under vacuum and extracted with 2 N sodium hydroxide. The basic aqueous solution was extracted with ether. The ether extract was concentrated under vacuum to yield 4.9 g of crude product, which was washed with hexane, leaving 1.9 g of white solid product of cyclohexanehydroxamic acid methyl ester.

EXAMPLE VI

Preparation of O-Ethyl-S-propyl-O-(1-methoxyethylidenamino)phosphorothioate (Method I)

A 40 g (44.9 mmol) quantity of acetohydroxamic methyl ester was dissolved in 85 ml of methylene chloride and cooled in an ice bath. To this mixture 6.4 ml (46 mmol) of triethylamine was added and the resulting mixture stirred at 25° C. for 30 minutes. 9.39 g (46 mmol) of O-ethyl-S-propylchlorophosphate dissolved in 15 ml of dichloromethane was then added dropwise. The reaction was stirred overnight at 25° C. Ether was added before filtration and the mixture was concentrated under vacuum. The resulting oil was dissolved in ether and washed successively with water, 1% aqueous hydrochloric acid, water, 2% sodium bicarbonate, saturated sodium chloride and dried with magnesium sulfate. The product was then concentrated to afford 10.1 g of crude product. Chromatography on silica gel yielded 6.7 g (58%) of O-ethyl-S-propyl-O-(1-methoxyethylidenamino)-phosphorothioate.

Calc'd for $C_8H_{18}NO_4PS$: C, 37.64; H, 7.11; N, 5.49. Found: C, 37.95; H, 7.36; N, 5.41.

O-Ethyl-S-propyl-O-(1-ethoxy-ethylidenamino) phosphorothioate can also be conveniently prepared according to method I as illustrated in Example VI, but may be purified with a sodium hydroxide wash.

Calc'd for $C_9H_{20}NO_4PS$: C, 40.15; H, 7.43; N, 5.20. Found: C, 40.53; H, 7.67; N, 5.62.

EXAMPLE VII

Preparation of O-Ethyl-S-propyl-O-(1-methoxyethylidenamino)-phosphorodithioate (Method I)

A 2.0 g (22.4 mmol) quantity of acetohydroxamic acid methyl ester was dissolved in 100 ml of acetonitrile. Added to this was 1.65 g (25 mmol) of 85% powdered potassium hydroxide followed by a catalytic amount of 18-crown-6-ether. The reaction mixture was stirred for twenty minutes at 25° C. After stirring, 5.47 g (25 mmol) of O-ethyl-S-propylchlorothiophosphate was added. The reaction mixture was stirred for two days at 25° C. and then filtered and concentrated under vacuum. The resulting product was dissolved in ether and washed successively with water, 1% aqueous hydrochloric acid, 2 N sodium hydroxide, water, and dried with anhydrous magnesium sulfate. The product was then concentrated under vacuum to yield 4.8 g of crude product which was chromatographed on silica gel to afford 3.6 g (59%) of O-ethyl-S-propyl-O-(1-methoxyethylidenamino)phosphorothioate.

Calc'd for $C_8H_{18}NO_3PS_2$: C, 35.41; H, 6.68; N, 5.16. Found: C, 35.68; H, 6.85; N, 5.09.

The following compounds are illustrative of this invention all of which can be conveniently prepared by the processes of this invention simply by selecting appropriate starting materials:

O-Ethyl-S-propyl-O-(5,5-dimethyl-2-methylimino-1,3-dithiolan-4-ylimino)phosphorothioate.
O-Ethyl-S-propyl-O-(5,5-dimethyl-2-methylimino-1,3-dithiolan-4-ylimino)phosphorodithioate.
O-Ethyl-S-propyl-O-(5,5-dimethyl-2-isopropylimino-1,3-dithiolan-4-ylimino)phosphorothioate.
O-Ethyl-S-propyl-O-(5,5-dimethyl-2-isopropylimino 1,3-dithiolan-4-ylimino)phosphorodithioate.
O-Ethyl-S-propyl-O-(5,5-dimethyl-2-sec-butylimino-1,3-dithiolan-4-ylimino)phosphorothioate.
O-Ethyl-S-butyl-O-(5,5-dimethyl-2-sec-butylimino-1,3-dithiolan-4-ylimino)phosphorothioate.
O-Ethyl-S-propyl-O-(5,5-dimethyl-2-tert-butylimino-1,3-dithiolan-4-ylimino)phosphorothioate.
O-Ethyl-S-propyl-O-(5,5-dimethyl-2-octylimino-1,3-dithiolan-4-ylimino)phosphorothioate.
O-Ethyl-S-propyl-O-(5,5-dimethyl-2-tert-octylimino-1,3-dithiolan-4-ylimino)phosphorothioate.
O-Ethyl-S-propyl-O-(5,5-dimethyl-2-(1,1-diethylpropynylimino)-1,3-dithiolan-4-ylimino)phosphorothioate.
O-Ethyl-S-propyl-O-(5,5-dimethyl-2-dimethylhydrazono-1,3-dithiolan-4-ylimino)phosphorothioate.
O-Ethyl-S-propyl-O-(5,5-dimethyl-2-cyanoimino-1,3-dithiolan-4-ylimino)phosphorothioate.
O-Ethyl-S-propyl-O-(5,5-dimethyl-2-methylsulfonylimino-1,3-dithiolan-4-ylimino)phosphorothioate.
O-Ethyl-S-propyl-O-(5,5-dimethyl-2-(4'-methylphenylsulfonylimino)-1,3-dithiolan-4-ylimino)phosphorothioate.
O-Ethyl-S-propyl-O-(5,5-dimethyl-2-(4'-methylphenylsulfonylimino)-1,3-dithiolan-4-ylimino)phosphorodithioate.
O-Ethyl-S-butyl-O-(5,5-dimethyl-2-(4'-methylphenylsulfonylimino)-1,3-dithiolan-4-ylimino)phosphorothioate.
O-Ethyl-S-propyl-O-(5,5-dimethyl-2-dicyanomethylidene-1,3-dithiolan-4-ylimino)phosphorothioate.
O-Ethyl-S-isopropyl-O-(5,5-dimethyl-2-dicyanomethylidene-1,3-dithiolan-4-ylimino)phosphorothioate.
O-Ethyl-S-propyl-O-(5,5-dimethyl-2-dicyanomethylidene-1,3-dithiolan-4-ylimino)phosphorodithioate.
O-Ethyl-S-propyl-O-(3,5,5-trimethyl-4-oxo-1,3-thiazolidin-2-ylimino)phosphorothioate.
O-Ethyl-S-isopropyl-O-(3,5,5-trimethyl-4-oxo-1,3-thiazolidin-2-ylimino)phosphorothioate.
O-Ethyl-S-propyl-O-(3,5,5-trimethyl-4-oxo-1,3-thiazolidin-2-ylimino)phosphorodithioate.
O-Ethyl-S-butyl-O-(3,5,5-trimethyl-4-oxo-1,3-thiazolidin-2-ylimino)phosphorothioate.
O-Ethyl-S-ethyl-O-(3,5,5-trimethyl-4-oxo-1,3-thiazolidin-2-ylimino)phosphorothioate.
O-Ethyl-S-propyl-O-(3-propyl-5,5-dimethyl-4-oxo-1,3-thiazolidin-2-ylimino)phosphorothioate.
O-Ethyl-S-isopropyl-O-(3-propyl-5,5-dimethyl-4-oxo-1,3-thiazolidin-2-ylimino)phosphorothioate.
O-Ethyl-S-propyl-O-(3-isopropyl-5,5-dimethyl-4-oxo-1,3-thiazolidin-2-ylimino)phosphorothioate.
O-Ethyl-S-propyl-O-(3-isopropyl-5,5-dimethyl-4-oxo-1,3-thiazolidin-2-ylimino)phosphorodithioate.
O-Ethyl-S-propyl-O-(3-allyl-5,5-dimethyl-4-oxo-1,3-thiazolidin-2-ylimino)phosphorothioate.
O-Ethyl-S-propyl-O-(3-(2-methylallyl)-5,5-dimethyl-4-oxo-1,3-thiazolidin-2-ylimino)phosphorothioate.
O-Ethyl-S-isopropyl-O-(3-(2-methylallyl)-5,5-dimethyl-4-oxo-1,3-thiazolidin-2-ylimino)phosphorothioate.
O-Ethyl-S-propyl-O-(3-(2-methoxyethyl)-5,5-dimethyl-4-oxo-1,3-thiazolidin-2-ylimino)phosphorothioate.
O-Ethyl-S-propyl-O-(3,5-dimethyl-4-oxo-1,3-thiazolidin-2-ylimino)phosphorothioate.
O-Ethyl-S-propyl-O-(3-isopropyl-5-methyl-4-oxo-1,3-thiazolidin-2-ylimino)phosphorothioate.
O-Ethyl-S-propyl-O-(3-isopropyl-4-oxo-1,3-thiazolidin-2-ylimino)phosphorothioate.

O-Ethyl-S-propyl-O-(3-isobutyl-4-oxo-1,3-thiazolidin-2-ylimino)phosphorothioate.
O-Ethyl-S-propyl-O-(3-allyl-4-oxo-1,3-thiazolidin-2-ylimino)phosphorothioate.
O-Ethyl-S-propyl-O-(3-(2-methylallyl)-4-oxo-1,3-thiazolidin-2-ylimino)phosphorothioate.
O-Ethyl-S-propyl-O-(3,5,5-trimethyl-4-thiono-1,3-thiazolidin-2-ylimino)phosphorodithioate.
O-Ethyl-S-propyl-O-(5-methyl-1,3-oxathiolan-4-ylimino)phosphorothioate.
O-Ethyl-S-butyl-O-(5-methyl-1,3-oxathiolan-4-ylimino)phosphorothioate.
O-Ethyl-S-propyl-O-(1,3-dithiolan-2-ylimino)phosphorothioate.
O-Ethyl-S-propyl-O-(3-methyl-tetrahydro-5-oxo-1,4-thiazin-2-ylimino)phosphorothioate.
O-Ethyl-S-propyl-O-(1,4-dithian-2-ylimino)phosphorothioate.
O-Ethyl-S-propyl-O-(2-methylimino-1,3-dithiolan-4-ylimino)phosphorothioate.
O-Ethyl-S-butyl-O-(5-hexyl-5-methyl-2-methylimino-1,3-dithiolan-4-ylimino)phosphorothioate.
O-Propyl-S-pentyl-O-(5-octyl-2-methylimino-1,3-dithiolan-4-ylimino)phosphorothioate.
O-Propyl-S-butyl-O-(2-dicyanomethylidene-1,3-dithiolan-4-ylimino)phosphorothioate.
O-Ethyl-S-sec-butyl-O-(3-methyl-5-octyl-4-oxo-1,3-thiazolidin-2-ylimino)phosphorothioate.
O-Ethyl-S-propyl-O-(3-hexyl-5,5-dimethyl-4-thiono-1,3-thiazolidin-2-ylimino)phosphorodithioate.
O-Ethyl-S-propyl-O-(tetrahydro-3-oxo-1,4-thiazin-2-ylimino)phosphorothioate.
O-Ethyl-S-propyl-O-(thiophan-2-ylimino)phosphorothioate.
O-Ethyl-S-propyl-O-(1,3-dithiolan-4-ylimino)phosphorothioate.
O-Ethyl-S-propyl-O-(5,5-dimethyl-1,3-dithiolan-4-ylimino)phosphorothioate.
O-Ethyl-S-propyl-O-(1-ethoxy-2-methylpropylidenamino)phosphorothioate.
O-Ethyl-S-propyl-O-(1-isopropoxypropylidenamino)phosphorothioate.
O-Ethyl-S-propyl-O-(1-methoxy-4'-methylthiobenzylidenamino)phosphorothioate.
O-Ethyl-S-propyl-O-(1-ethoxy-2-methoxyethylidenamino)phosphorothioate.
O-Ethyl-S-propyl-O-(1-butoxy-4'-chlorobenzylidenamino)phosphorothioate.
O-Ethoxy-S-propyl-O-(1-methoxy-4'-methylbenzylidenamino)phosphorothioate.
O-Ethyl-S-propyl-O-(1-ethoxycyclohexylmethylideneamino)phosphorodithioate.
O-Ethyl-S-propyl-O-(1-methoxycyclopentylmethylideneamino)phosphorothioate.
O-Ethyl-S-propyl-O-(1-methoxynonylideneamino)phosphorothioate.
O-Ethyl-S-propyl-O-(1-ethoxycyclopropylmethylidenamino)phosphorothioate.
O-Ethyl-S-butyl-O-(1-ethoxy-2,2-dimethylpropylidenamino)phosphorothioate.

Selected species of the new compounds were evaluated to determine their pesticidal activity against mites, mite eggs, an aphid, a caterpillar, a beetle, a fly and a nematode.

Suspensions of the test compounds were prepared by dissolving one gram of compound in 50 ml of acetone in which had been dissolved 0.1 g (10 percent of the weight of the compound) of an alkylphenoxy polyethoxyethanol surfactant, as an emulsifying or dispersing agent. The resulting solution was mixed into 150 ml of water to give roughly 200 ml of a suspension containing the compound in finely divided form. The thus-prepared stock suspension contained 0.5 percent by weight of compound. The concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 68°–70° F. and 50±5 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids were placed on a revolving turntable and sprayed with 100–110 milliliters of test compound formulation by use of a DeVilbiss spray gun set at 40 psig air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 68°–70° F. and 50±5 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Bait Test

Larvae of the southern armyworm (*Spodoptera eridania*, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Tendergreen bean plants of standard height and age were placed on a revolving turntable and sprayed with 100-110 milliliters of test compound formulation by use of a DeVilbiss spray gun set at 40 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for three days. Although the larvae could easily consume the leaf within 24 to 48 hours, no more food was added. Larvae which were unable to move the length of the body, even upon stimulation, were considered dead.

Southern Armyworm Ovicide Test

The test organism was the egg of the Southern armyworm (*Spodoptera eridania* (Cram.)) as obtained from adults reared on Tendergreen bean plants at a temperature of 80°±5° F. and a relative humidity of 50±5 percent. The eggs were laid on freezer paper (Marlon 717, Copco paper). The paper was then cut into small sections containing one or two egg masses.

The test compounds were formulated by diluting the stock suspension with water to give a suspension containing 500 parts of test compound per million parts of final formulation. The egg masses were dipped until they were thoroughly wet (5-10 seconds). They were then placed on a paper towel face up and were allowed to dry for 15-30 minutes. The dry eggs were placed in a 15×60 mm petri dish containing a cotton dental wick saturated with a 5 percent sodium chloride solution to maintain a high level of humidity. The closed dishes were labeled and held at a temperature of 80°±5° F. for four days. Larvae that emerged from the eggs, even if dead at the time of observation, were recorded as hatched.

Mite Foliage Spray Test

Adults and nymphal stage of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 mites, a sufficient number for testing, were transferred from the excised leaves to the fresh plants in a period of twenty-four hours. Following the twenty-four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which last 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

Mite Ovicide Test

The test organism was the egg of two-spotted mite (*Tetranychus urticae* Koch) as obtained from adults reared on Tendergreen bean plants under controlled conditions of 80°±5° F. and 50±5 percent relative humidity. Heavily infested leaves from a stock culture were placed on the primary leaves of 2 bean plants 6 to 8 inches in height, growing in a 2½ inch clay pot. Females were allowed to oviposit for a period of 48 hours and then the leaves of the infested plants were dipped in a solution containing 800 parts of tetraethyl pyrophosphate per million parts of water in order to destroy the reproductive forms and thus prevent further egg-laying. This solution of tetraethyl pyrophosphate does not affect the viability of the eggs. The plants were allowed to dry thoroughly.

The potted plants (one pot per compound) were placed on a revolving turntable and sprayed with 100-110 milliliters of test compound formulation by use of a DeVilbiss spray gun set at 40 psig air pressure. This application, which lasted 30 seconds, was sufficient to wet the plants to run-off. As a control, 100-110 milliliters of a water solution containing acetone and emulsifier in the same concentrations as the test compound formulation, but containing no test compound, were also sprayed on plants infested with eggs. The sprayed plants were held at 80°±5° F. and 50±5 percent relative humidity for 6 days, after which a microscopic examination was made of unhatched (dead) and hatched (living) eggs. Percent mortality was recorded for various concentration levels.

Fly Bait Test

Four to six day old adult house flies (*Musca domestica*, L.), reared according to the specifications of the Chemical Specialities Manufacturing Association (Blue Book, McNair-Dorland Co., N.Y. 1954; pages 243-244, 261) under controlled conditions of 80°±5° F. and 50±5 percent relative humidity, were the test insects. The flies were immobilized by anesthetizing with carbon dioxide and twenty-five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the good strainer prior to admitting the anesthetized flies. The caged flies were allowed to feed on the bait for twenty-four hours, at a temperature of 80±5 F. and a relative humidity of 50± percent. Flies which showed no sign of movement on prodding were considered dead.

Nematocide Test

The test organism used was the infective migratory larvae of the root-knot nematode, *Meloidogyne incognita var. acrita*, reared in the greenhouse on roots of cucumber plants. Infected plants were removed from the culture, and the roots chopped very finely. A small amount of this inoculum was added to a pint jar containing approximately 180 cc. of soil. The jars were capped and incubated for one week at room temperature. During this period eggs of the nematode were hatched, and the larval forms migrated into the soil.

Ten ml. of the test formulation were added to each of the two jars for each dosage tested. Following the addition of chemical, the jars were capped, and the contents thoroughly mixed on a ball mill for 5 minutes.

The test compounds were formulated by a standard procedure of solution in acetone, addition of an emulsifier, and dilution with water. Primary screening tests were conducted at 3.33 mg. of the test compound per jar.

The jars were left capped at room temperature for a period of 48 hours, and the contents then transferred to 3 inch pots. Subsequently, the pots were seeded to cucumber as an indicator crop and placed in the greenhouse where they were cared for in the normal fashion for approximately 3 weeks.

The cucumber plants were then taken from the pots, the soil removed from the roots, and the amount of galling visually rated.

The results of these tests together with physical properties of the tested compounds are set forth in Table I below. In these tests the pesticidal activity of the compounds at the indicated dosage rate against aphid, mite, Southern Armyworm, Bean Beetle, housefly and was rated as follows:

A = excellent control
B = partial control
C = no control at 500 ppm.

In the test for activity against nematodes activity was rated as follows:

1 = severe galling, equal to untreated plants
2 = moderate galling
3 = light galling
4 = very light galling
5 = no galling, perfect control
Dashes indicate no test conducted.

The compounds contemplated in this invention may be applied as insecticides, miticides and nematocides according to methods known to those skilled in the art. Pesticidal compositions containing the compounds as the active toxicant will usually comprise a carrier and-/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Non-ionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein control the population of insects, nematodes, mites and mite and insect ova upon plants or other material to which the pesticides are applied. Certain of the compounds of this invention, particularly the nonheterocyclic compounds, possess fumigant properties. Generally, when used in sufficient amount to kill or repel the insects, they do not burn or injure the plant. The toxicants are compatible with substantially any other constituents of the spray schedule, and they may be used in the soil, upon the seeds, or the roots of plants without injuring either the seeds or roots of plants. They may also be used in combination with other pesticidally active compounds.

TABLE I

Biological and Analytical Properties of the Compounds of this Invention

| | Spectral Data Elemental Analysis/NMR | Biological Activity | | | | | |
|---|---|---|---|---|---|---|---|
| | | Bean Aphid | Mite | Southern Armyworm | Mexican Bean Beetle | Housefly | Nematode |
| O-Ethyl-S-propyl-O-(5,5-dimethyl-2-methylimino-1,3-dithiolan-4-ylimino)-phosphorothioate | (CDCl$_3$)δ4.58-3.98(m,2H, OCH$_2$);3.42-2.60(m,5H); 2.05-0.83(m,14H) | A | A | A | B | A | 1 |

TABLE I-continued

Biological and Analytical Properties of the Compounds of this Invention

| | Spectral Data Elemental Analysis/NMR | Bean Aphid | Mite | Southern Armyworm | Mexican Bean Beetle | House-fly | Nema-tode |
|---|---|---|---|---|---|---|---|
| O-Ethyl-S-propyl-O(5,5-dimethyl-2-methylimino-1,3-dithiolan-4-ylimino)phosphorodithioate | (CDCl$_3$)δ4.63-3.98(m,2H, OCH$_2$);3.39-2.65(m,5H); 2.03-0.82(m,14H) | A | A | A | A | A | 1 |
| O-Ethyl-S-propyl-O-(5,5-dimethyl-2-isopropylimino-1,3-dithiolan-4-ylimino)phosphorothioate | (CDCl$_3$)δ4.60-3.96(m,2H, OCH$_2$);3.61-2.59(m,3H); 1.98-0.82(m,20H) | A | A | A | A | A | 3 |
| O-Ethyl-S-propyl-O(5,5-dimethyl-2-isopropylimino 1,3-dithiolan-4-ylimino)phosphorodithioate | (CDCl$_3$)δ4.65-4.00(m,2H, OCH$_2$);3.70-2.60(m,3H); 2.15-0.75(m,20H) | A | A | A | A | A | 1 |
| O-Ethyl-S-propyl-O-(5,5-dimethyl-2-sec-butylimino-1,3-dithiolan-4-ylimino)phosphorothioate | (CDCl$_3$)δ4.60-3.86(m,2H, OCH$_2$);3.40-2.52(m,3H); 2.05-0.80(m,22H) | A | A | A | A | A | 5 |
| O-Ethyl-S-butyl-O-(5,5-dimethyl-2-sec-butylimino-1,3-dithiolan-4-ylimino)phosphorothioate | (CDCl$_3$)δ4.53-3.97(m,2H, OCH$_2$);3.42-2.46(m,3H); 1.98-0.68(m,24H) | A | A | A | A | A | 1 |
| O-Ethyl-S-propyl-O-(5,5-dimethyl-2-tert-butylimino-1,3-dithiolan-4-ylimino)phosphorothioate (C$_{14}$H$_{27}$N$_2$O$_3$PS$_3$) | Found: C,42.59;H,6.87 | A | A | A | A | A | 1 |
| O-Ethyl-S-propyl-O-(5,5-dimethyl-2-octylimino-1,3-dithiolan-4-ylimino) phosphorothioate | (CDCl$_3$)δ4.50-3.92(m, 2H, OCH$_2$);3.68-2.53 (m,4H);2.03-0.65(m,29H) | C | A | A | A | A | 1 |
| O-Ethyl-S-propyl-O-(5,5-dimethyl-2-tert-octylimino-1,3-dithiolan-4-ylimino) phosphorothioate | (CDCl$_3$)δ4.53-3.84(m, 2H,OCH$_2$);3.60-2.49 (m,2H, SCH$_2$);2.10-0.78 (m,31H) | C | A | C | C | A | 1 |
| O-Ethyl-S-butyl-O-(5,5-dimethyl-2-(4'-1-ethylphenylsulfonylimino)-1,3-dithiolan-4-ylimino)phosphorothioate (C$_{18}$H$_{27}$N$_2$O$_5$PS$_4$) | Found:C,43.20;H,5.65 | C | A | A | A | B | 1 |
| O-Ethyl-S-propyl-O-(5,5-dimethyl-2-dicyanomethylidene-1,3-dithiolan-4-ylimino) phosphorothioate (C$_{13}$H$_{18}$N$_3$O$_3$PS$_3$) | Found:C,40.37;H,4.73 | A | A | A | B | A | |
| O-Ethyl-S-isopropyl-O-(5,5-dimethyl-2-dicyanomethylidene-1,3-dithiolan-4-ylimino) phosphorothioate (C$_{13}$H$_{18}$N$_3$O$_3$PS$_3$) | Found:C,39.87;H,4.81 | C | A | A | B | A | |
| O-Ethyl-S-propyl-O-(5,5-dimethyl-2-dicyanomethylidene-1,3-dithiolan-4-ylimino) phosphorodithioate (C$_{13}$H$_{18}$N$_3$O$_2$PS$_4$) | Found:C,38.42;H,4.53 | C | A | A | B | A | 1 |
| O-Ethyl-S-propyl-O-(3,5,5-trimethyl-4-oxo-1-thiazolidin-2-ylimino)-phosphorothioate | (CDCl$_3$)δ4.51-3.90 (m,2H,OCH$_2$);3.38-2.51 (m,5H);2.00-0.81(m,14H) | A | A | A | A | A | 1 |
| O-Ethyl-S-isopropyl-O-(3,5,5-trimethyl-4 oxo-1,3-thiazolidin-2-ylimino) phosphorothioate | (CDCl$_3$)δ4.64-3.81(m, 3H);3.26(S,3H);2.28-0.79(m,15H) | B | A | A | C | A | 1 |
| O-Ethyl-S-propyl-O-(3,5,5-trimethyl-4-oxo-1,3-thiazolidin-2-ylimino)-phosphorodithioate (C$_{11}$H$_{21}$N$_2$O$_3$PS$_3$) | Found:C,36.87;H.6.04 | A | A | A | A | A | 5 |
| O-Ethyl-S-propyl-O-(5,5-dimethyl-2-(1,1-diethylpropynylimino)-1,3-dithiolan-4-ylimino)phosphorothioate | (CDCl$_3$)δ4.55-3.95(m,2H, OCH$_2$);3.30-2.70(m,2H,5CH$_2$); 2.15-0.85(m,25H) | C | A | A | A | A | —** |
| O-Ethyl-S-propyl-O-(5,5-dimethyl-2-dimethylhydrazono-1,3-dithiolan-4-ylimino)phosphorothioate (C$_{12}$H$_{24}$N$_3$O$_3$PS$_3$) | Found:C,37.49;H,6.34 | A | A | A | A | A | 1 |
| O-Ethyl-S-propyl-O-(5,5-dimethyl-2-cyanoimino-1,3-dithiolan-4-ylimino) phosphorothioate | (CDCl$_3$)δ4.45-3.95(m,2H,OCH$_2$); 3.15-2.55(m,2H,SCH$_2$);1.95-0.80(m,14H) | C | A | B | B | A | 1 |
| O-Ethyl-S-propyl-O-(5,5-dimethyl-2-methylsulfonylimino-1,3-dithiolan-4-ylimino)phosphorothioate | (CDCl$_3$)δ4.65-3.85(m,2H, OCH$_2$); 3.35-2.53(m,5H):2.10-0.75 (m,14H) | C | A | A | A | A | 1 |
| O-Ethyl-S-propyl-O-(5,5-dimethyl-2-(4'-methylphenylsulfonylimino)-1,3-dithiolan-4-ylimino)phosphorothioate | (CDCl$_3$)δ8.07-7.11(m,4H, aromatic);4.49-3.84(m,2H, OCH$_2$);3.23-2.52(m,2H,SCH$_2$); 2.50-0.78(m,17H) | C | A | B | A | A | 1 |
| O-Ethyl-S-butyl-O-(3,5,5-trimethyl-4-oxo-1,3-thiazolidin-2-ylimino)phosphorothioate C$_{12}$H$_{23}$N$_2$O$_4$PS$_2$) | Found:C,40.61;H,6.53 | A | A | A | A | A | 1 |
| O-Ethyl-S-ethyl-O-(3,5,5-trimethyl-4-oxo-1,3-thiazolidin-2-ylimino)phosphorothioate (C$_{10}$H$_{19}$N$_2$O$_4$PS$_2$) | Found:C,37.44;H,6.20 | C | A | C | C | A | 1 |
| O-Ethyl-S-propyl-O-(3-propyl-5,5-dimethyl-4-oxo-1,3-thiazolidin-2-ylimino)phosphoro-thioate (C$_{13}$H$_{25}$N$_2$O$_4$PS$_2$) | Found:C,42.89;H,6.99 | A | A | A | A | A | 5 |
| O-Ethyl-S-isopropyl-O-(3-propyl-5,5-dimethyl-4-oxo-1,3-thiazolidin-2-ylimino) phosphorothioate | (CDCl$_3$)δ4.47-3.51(m,6H); 1.98-0.76(m,17H) | A | A | A | B | A | 1 |

TABLE I-continued

Biological and Analytical Properties of the Compounds of this Invention

| | Spectral Data Elemental Analysis/NMR | Bean Aphid | Mite | Southern Armyworm | Mexican Bean Beetle | House-fly | Nematode |
|---|---|---|---|---|---|---|---|
| O-Ethyl-S-propyl-O-(3-isopropyl-5,5-dimethyl-4-oxo-1,3-thiazolidin-2-ylimino)phosphorothioate ($C_{13}H_{25}N_2O_4PS_2$) | Found:C,42.0;H,7.0 | A | A | A | A | A | 4 |
| O-Ethyl-S-propyl-O-(3-isopropyl-5,5-dimethyl-4-oxo-1,3-thiazolidin-2-ylimino)phosphorodithioate ($C_{13}H_{25}N_2O_3PS_3$) | Found:C,41.15;H,6.54 | A | A | A | A | A | 1 |
| O-Ethyl-S-propyl-1-O-(3-allyl-5,5-dimethyl-4-oxo-1,3-thiazolidin-2-ylimino)phosphorothioate ($C_{13}H_{23}N_2O_4PS_2$) | Found:C,42.45;H,6.50 | A | A | A | A | A | 1 |
| O-Ethyl-S-propyl-O-(3-(2-methylallyl)-5,5-dimethyl-4-oxo-1,3-thiazolidin-2-ylimino)phosphorothioate ($C_{14}H_{25}N_2O_4PS_2$) | Found:C,44.61;H,6.87 | A | A | A | A | A | 1 |
| O-Ethyl-S-isopropyl-O-(3-(2-methylallyl)-5,5-dimethyl-4-oxo-1,3-thiazolidin-2-ylimino)phosphorothioate ($C_{14}H_{25}N_2O_4PS_2$) | Found:C,44.84;H,6.83 | C | A | A | C | A | 1 |
| O-Ethyl-S-propyl-O-(3-(2-methoxyethyl)-5,5-dimethyl-4-oxo-1,3-thiazolidin-2-ylimino)phosphorothioate ($C_{13}H_{25}N_2O_5PS_2$) | Found:C,40.24;H,6.85 | A | A | A | A | A | 5 |
| O-Ethyl-S-propyl-O-(3,5-dimethyl-4-oxo-1,3-thiazolidin-2-ylimino)phosphorothioate | (CDCl$_3$)δ4.60-3.82(m,3H); 3.15-2.54(m,5H);2.16-0.80(m,11H) | A | A | A | A | A | 4 |
| O-Ethyl-S-propyl-O-(3-isopropyl-5-dimethyl-4-oxo-1,3-thiazolidin-2-ylimino)phosphorothioate | (CDCl$_3$)δ4.95-3.55(broad,4H); 3.26-2.51(m,2H,SCH$_2$);1.90-0.82(m,17H) | A | A | A | A | A | 4 |
| O-Ethyl-5-propyl-O-(3-isopropyl-4-oxo-1,3-thiazolidin-2-ylimino)phosphorothioate | (CDCl$_3$)δ4.90-3.85(m,3H); 3.68-3.22(q,2H);3.20-2.45(m,2H,SCH$_2$);2.10-0.73(m,14H) | B | A | B | A | A | 3 |
| O-Ethyl-S-propyl-O-(3-isobutyl-4-oxo-1,3-thiazolidin-2-ylimino)phosphorothioate | (CDCl$_3$)δ4.59-3.95(m,2H);3.82(S,2H);3.72-2.64(m,5H);1.98-0.77(m,14H) | B | A | B | B | A | 1 |
| O-Ethyl-S-propyl-O-(3-allyl-4-oxo-1,3-thiazolidin-2-ylimino)phosphorothioate | (CDCl$_3$)δ6.35-5.13(m,3H, vinyl);4.65-3.75(m,6H); 3.30-2.60(m,2H,SCH$_2$);2.05-0.82(m,8H) | B | A | A | A | A | 1 |
| O-Ethyl-S-propyl-O-(3-(2-methylallyl)-4-oxo-1,3-thiazolidin-2-ylimino)phosphorothioate ($C_{12}H_{21}N_2O_4PS_2$) | Found:C,40.44;H,6.03 | A | A | A | A | A | 4 |
| O-Ethyl-S-propyl-O-(3,5,5-trimethyl-4-thiono-1,3-thiazolidin-2-ylimino)phosphorothioate ($C_{11}H_{21}N_2O_3PS_3$) | Found:C,37.17;H,5.96 | A | A | A | A | A | 5 |
| O-Ethyl-S-propyl-O-(5-methyl-1,3-oxathiolan-4-ylimino)phosphorothioate | (CDCl$_3$)δ5.26(g,2H); 4.84-3.88(m,3H);3.22-2.53(m,2H,SCH$_2$);1.98-0.82(m,11H) | A | A | B | B | A | 1 |
| O-Ethyl-S-butyl-O-(5-methyl-1,3-oxathiolan-4-ylimino)phosphorothioate ($C_{10}H_{20}NO_4PS_2$) | Found:C,37.88;H,6.40 | A | A | C | C | A | 1 |
| O-Ethyl-S-propyl-O-(5-methyl-1,3-oxathiolan-4-ylimino)phosphorodithioate ($C_9H_{18}NO_3PS_3$) | Found:C,34.76;H,5.85 | A | A | A | A | A | 1 |
| O-Ethyl-S-ethyl-O-(5-methyl-1,3-oxathiolan-4-ylimino)phosphorodithioate ($C_8H_{16}NO_4PS_2$) | Found:C,33.69;H,5.83 | C | A | C | A | A | 1 |
| O-Ethyl-S-propyl-O-(1,4-dithian-2-ylimino)phosphorothioate | (CDCl$_3$)δ4.58-4.00(m,2H,OCH$_2$);3.59(s,2H); 3.29-2.62(m,6H);1.99-0.83(m,8H) | A | A | A | B | A | 1 |
| O-Ethyl-S-propyl-O-(1-methoxy ethylideneamino)phosphorothioate ($C_8H_{18}NO_4PS$) | Found:C,37.95;H,7.36 | C | A | A | A | A | 5 |
| O-Ethyl-S-propyl-O-(1-ethoxyethylidenamino)phosphorothioate | (CDCl$_3$)δ4.49-3.86(m,4H); 3.25-2.52(m,2H,SCH$_2$);2.05(s,3H)1.90-0.82(m,11H) | A | A | A | A | A | 5 |
| O-Ethyl-S-propyl-O-(1-isopropoxyethylidenamino)phosphorothioate ($C_{10}H_{22}NO_4PS \cdot H_2O$) | Found:C,39.43;H,7.86 | A | A | C | A | A | |
| O-Ethyl-S-propyl-O-(1-methoxy-2,2-dimethylpropylidenamino)phosphorothioate ($C_{11}H_{24}NO_4PS$) | Found:C,43.87;H,8.14 | A | A | A | A | A | |
| O-Ethyl-S-propyl-O-(1-ethoxy-2,2-dimethylpropylidenamino)phosphorothioate ($C_{12}H_{26}NO_4PS$) | Found:C,46.19;H,8.60 | A | A | A | A | A | |
| O-Ethyl-S-propyl-O-(1-isopropoxy-2,2- | Found:C,45.86;H, | | | | | | |

TABLE I-continued

Biological and Analytical Properties of the Compounds of this Invention

| | Spectral Data Elemental Analysis/NMR | Bean Aphid | Mite | Southern Armyworm | Mexican Bean Beetle | House-fly | Nematode |
|---|---|---|---|---|---|---|---|
| dimethylpropylidenamino)phosphorothioate ($C_{13}H_{28}NO_4PS \cdot H_2O$) | 8.49 | A | C | C | C | C | |
| O-Ethyl-S-propyl-O-(1-methoxybenzylidenamino)phosphorothioate ($C_{13}H_{20}NO_4PS \cdot H_2O$) | Found:C,46.58;H,6.67 | A | A | A | A | A | |
| O-Ethyl-S-propyl-O-(1-ethoxybenzylidenamino)phosphorothioate ($C_{14}H_{22}NO_4PS$) | Found:C,50.51;H,7.06 | A | A | A | A | A | |
| O-Ethyl-S-propyl-O-(1-isopropoxybenzylidenamino)phosphorothioate ($C_{15}H_{24}NO_4PS$) | Found:C,52.88;H,7.22 | A | A | C | A | A | |
| O-Ethyl-S-propyl-O-(1-methoxycyclohexylmethylidenamino)phosphorothioate ($C_{13}H_{26}NO_4PS$) | Found:C,47.48;H,8.25 | A | A | C | C | A | 3 |
| O-Ethyl-S-propyl-O-(1-ethoxycyclohexylmethylidenamino)phosphorothioate ($C_{14}H_{28}NO_4PS$) | Found:C,50.12;H,8.64 | C | C | C | A | C | 1 |
| O-Ethyl-S-propyl-O-(1-methoxylidenamino)phosphorothioate ($C_8H_{18}NO_3PS_2$) | Found:C,35.68;H,6.85 | A | A | B | B | B | 5 |
| O-Ethyl-S-propyl-O-(1-ethoxyethylidenamino)phosphorodithioate ($C_9H_{20}NO_3PS_2$) | Found:C,37.92;H,7.39 | C | A | B | A | A | 5 |

**A dash indicates no test was conducted.

What is claimed is:

1. Compounds of the formula:

$$R=N-O-\underset{\underset{SR_4}{|}}{\overset{\overset{X}{\|}}{P}}-OR_3$$

wherein:
X is oxygen or sulfur;
R$_3$ and R$_4$ are individually alkyl; provided that the total number of aliphatic carbon atoms in each of R$_3$ and R$_4$ does not exceed six;
R is:

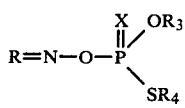

a.

wherein:
R$_1$ is alkyl, cycloalkyl or phenyl, all of which may be unsubstituted or substituted with one or more alkyl, halogen, alkoxy, or alkylthio substituents; provided that the total number of aliphatic carbon atoms in any alkyl, alkoxy or alkylthio substituent may not exceed eight; and provided further that the total number of aliphatic carbon atoms in R$_1$ may not exceed sixteen; and provided further that when R$_1$ is cycloalkyl, the total number of aliphatic carbon atoms in said cycloalkyl ring structure may be no less than three and may not exceed six;
R$_2$ is alkyl, provided that the total number of aliphatic carbon atoms in R does not exceed eight; or

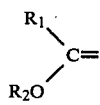

b.

wherein:

A is a three or four-membered divalent aliphatic chain, which may be optionally substituted by one or more alkyl or acyl groups each containing no more than six carbon atoms, and which may include in said chain one or more divalent:
sulfur, sulfinyl, sulfonyl, oxygen, carbonyl, thiono or dicyanomethylidene moieties; or
amino moieties, which may be optionally substituted with alkyl, alkenyl, alkoxyalkyl or acyl groups having no more than six carbon atoms; or
imino moeties of the formula:

wherein Y is alkyl, alkenyl, alkynyl, dialkylamino, cyano, alkylsulfonyl, aryl or arysulfonyl groups, aryl groups being optionally substituted with halogen or alkyl substitutents having no more than ten carbon atoms.

2. A compound in accordance with claim 1 wherein X is oxygen.

3. A compound in accordance with claim 1 wherein X is sulfur.

4. A compound in accordance with claim 1 wherein R$_3$ is ethyl and R$_4$ is propyl.

5. Compounds of the formula:

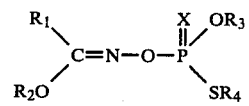

wherein:
X is either oxygen or sulfur;
R$_1$ is alkyl, cycloalkyl or phenyl, all of which may be unsubstituted or substituted with one or more alkyl, halogen, alkoxy or alkylthio substituents; provided that the total number of aliphatic carbon atoms in any alkyl, alkoxy or alkylthio substituent may not exceed eight; and provided further that the total number of aliphatic carbon atoms in $R_1$ may not exceed sixteen; and provided further that when $R_1$ is cycloalkyl, the total number of aliphatic carbon atoms in said cycloalkyl ring structure may be no less than three and may not exceed six;

$R_2$ is alkyl, provided that the total number of aliphatic carbon atoms in $R_2$ does not exceed eight;

$R_3$ and $R_4$ are individually alkyl.

6. A compound in accordance with claim 5 wherein $R_1$ is alkyl.

7. A compound in accordance with claim 5 wherein $R_1$ is phenyl substituted with alkyl moieties.

8. A compound in accordance with claim 5 wherein $R_2$ is methyl.

9. A compound in accordance with claim 5 wherein $R_2$ is ethyl.

10. Compounds of the formula:

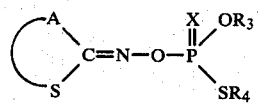

wherein:
X is oxygen or sulfur;
$R_3$ and $R_4$ are individually alkyl;
A is a three or four-membered divalent aliphatic chain, which may be optionally substituted by one or more alkyl groups each containing no more than six carbon atoms, and which may include in said chain one or more divalent:
  sulfur, sulfinyl, sulfonyl, oxygen, carbonyl, thiono or dicyanomethylidene moieties; or
  amino moieties, which may be optionally substituted with alkyl, alkenyl, alkoxyalkyl, or acyl groups having no more than six carbon atoms; or
  imino moieties of the formula:

wherein Y is alkyl, alkenyl, alkynyl, dialkylamino, cyano, alkylsulfonyl, aryl or arysulfonyl groups, said aryl groups being optionally substituted with halogen or alkyl substituents having no more than ten carbon atoms.

11. A compound in accordance with claim 10 wherein A is a three or four-membered divalent chain which may include one or more
  sulfur or oxygen atoms; or
  nitrogen atoms which are optionally substituted with alkyl, alkenyl, alkoxyalkyl, or acyl groups containing no more than six aliphatic carbon atoms; or
carbon atoms which are optionally substituted with an oxo or dicyanomethylidene moiety; or
  an imino moiety which may be substituted with alkyl or dialkylamino groups containing no more than ten carbon atoms; or one or more alkyl groups containing no more than six carbon atoms.

12. A compound in accordance with claim 10 wherein A, C and S complete a 2-oximino-1,4-dithiane; 2-oximino-1,3-dithiane; 4-oximino-1,3-dithiolane; 2-oximino-tetrahydro-1,4-thiazine-3-one; 2-oximino-1,3-dithiolane; 2-dicyanomethylidene-4-oximino-1,3-dithiolane; 2-oximinothiophanes; 4-oximino-1,3-oxathiolane; 5-oximino-1,3-thiazolidin-4-one, 2-oximino-1,3-thiazolidin-4-one; 2-oximino-tetrahydro-1,4-thiazine; 2-oximino-4-thiono-1,3-thiazolidene; 2-oximino-tetrahydro-1,4-thiazin-5-one ring structure; wherein said 2-oximino-tetrahydro-1,4-thiazine ring may be substituted by an acyl substituent on its nitrogen moiety.

13. A compound in accordance with claim 10 wherein A, C and S complete a 2-oximino-1,3-thiazolidin-4-one ring structure substituted with alkyl groups.

14. A compound in accordance with claim 10 wherein A, C and S complete a 2-oximino-1,3-thiazolidin-4-one ring structure substituted with alkenyl moieties.

15. A compound in accordance with claim 10 wherein A, C and S complete a 2-oximino-1,3-thiazolidin-4-one ring structure substituted with alkoxyalkyl moieties.

16. A compound in accordance with claim 10 wherein A, C and S complete a 2-imino-1,3-dithiolane-5-oximino ring structure substituted with alkyl groups and wherein said imino nitrogen is substituted with alkyl groups.

17. A compound in accordance with claim 10 wherein A, C and S complete a 2-imino-1,3-dithiolane-5-oximino ring structure and wherein said imino nitrogen is substituted with dialkylamino groups.

18. O-Ethyl-S-propyl-O-(1-methoxyethylidenamino)-phosphorothioate.

19. O-Ethyl-S-propyl-O-(1-ethoxyethylidenamino)-phosphorothioate.

20. O-Ethyl-S-propyl-O-(1-ethoxybenzylidenamino)-phosphorothioate.

21. O-Ethyl-S-propyl-O-(5,5-dimethyl-2-isopropylamino-1,3-dithiolan-4-ylimino)phosphorothioate.

22. O-Ethyl-S-propyl-O-(5,5-dimethyl-2-sec-butylimino-1,3-dithiolan-4-ylimino)phosphorothioate.

23. O-Ethyl-S-propyl-O-(5,5-dimethyl-2-tert-butylimino-1,3-dithiolan-4-ylimino)phosphorothioate.

24. O-Ethyl-S-propyl-O-(5,5-dimethyl-2-dimethylhydrazono-1,3-dithiolan-4-ylimino)phosphorothioate.

25. An insecticidal, miticidal and nematocidal composition comprising an acceptable carrier and as the active toxicant a pesticidally effective amount of a compound of the formula:

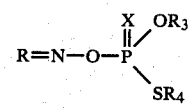

wherein:
X is oxygen or sulfur;
$R_3$ and $R_4$ are individually alkyl; provided that the total number of aliphatic carbon atoms in each of $R_3$ and $R_4$ does not exceed six;
R is:

a.

wherein:
$R_1$ is alkyl, cycloalkyl or phenyl, all of which may be unsubstituted or substituted with one or more alkyl, halogen, alkoxy or alkylthio substituents; provided that the total number of aliphatic carbon atoms in any alkyl, alkoxy or alkylthio substituent may not exceed eight; and provided further that the total number of aliphatic carbon atoms in $R_1$ may not exceed sixteen; and provided further that when $R_1$ is cycloalkyl, the total number of aliphatic carbon atoms in said cycloalkyl ring structure may be no less than three and may not exceed six;

$R_2$ is alkyl, provided that the total number of aliphatic carbon atoms in $R_2$ does not exceed eight; or b. 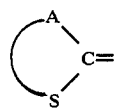

wherein:

A is a three- or four-membered divalent aliphatic chain, which may be optionally substituted on one or more alkyl groups each containing no more than six carbon atoms, and which may include in said chain one or more divalent;

sulfur, sulfinyl, sulfonyl, oxygen, carbonyl, thiono or dicyanomethylidene moieties; or amino moieties, which may be optionally substituted with alkyl, alkenyl, alkoxyalkyl, or acyl groups having no more than six carbon atoms; or imino moieties of the formula:

wherein Y is alkyl, alkenyl, alkynyl, dialkylamino, cyano, alkylsulfonyl, aryl or arysulfonyl groups, said aryl groups being optionally substituted with halogen or alkyl substituents having no more than ten carbon atoms.

26. A composition in accordance with claim 25 wherein X is oxygen.

27. A composition in accordance with claim 25 wherein X is sulfur.

28. A composition in accordance with claim 25 wherein $R_3$ is ethyl and $R_4$ is propyl.

29. An insecticidal, miticidal and nematocidal composition comprising an acceptable carrier and as the active toxicant an insecticidally, miticidally or nematocidally effective amount of a compound of the formula:

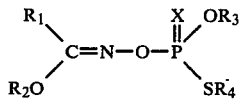

wherein:

X is either oxygen or sulfur;

$R_1$ is alkyl, cycloalkyl or phenyl, all of which may be unsubstituted or substituted with one or more alkyl, halogen, alkoxy or alkylthio substituents; provided that the total number of aliphatic carbon atoms in any alkyl, alkoxy or alkylthio substituent may not exceed eight; and provided further that the total number of aliphatic carbon atoms in $R_1$ may not exceed sixteen; and provided further than when $R_1$ is cycloalkyl, the total number of aliphatic carbon atoms in said cycloalkyl ring structure may be no less than three and may not exceed six;

R is alkyl, provided that the total number of aliphatic carbon atoms in $R_2$ does not exceed eight.

$R_3$ and $R_4$ are individually alkyl.

30. A composition in accordance with claim 29 wherein the active toxicant is O-Ethyl-S-propyl-O-(1-methoxyethylidenamino) phosphorothioate.

31. A composition in accordance with claim 29 wherein the active toxicant is O-Ethyl-S-propyl-O-(1-ethoxyethylidenamino) phosphorothioate.

32. A composition in accordance with claim 29 wherein the active toxicant is O-Ethyl-S-propyl-O-(1-ethoxybenzylidenamino) phosphorothioate.

33. An insecticidal and miticidal composition comprising an acceptable carrier and as the active toxicant an insecticidally or miticidally effective amount of a compound of the formula:

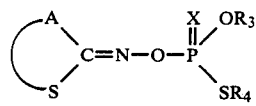

wherein:

X is oxygen or sulfur;

$R_3$ and $R_4$ are individually alkyl;

A is a three- or four-membered divalent aliphatic chain, which may be optionally substituted by one or more alkyl groups each containing no more than six carbon atoms, and which may include in said chain one or more divalent:

sulfur, sulfinyl, sulfonyl, oxygen, carbonyl, thiono or dicyanomethylidene moieties; or amino moieties which may be optionally substituted with alkyl, alkenyl, alkoxyalkyl or acyl groups having no more than six carbon atoms; or imino moieties of the formula:

wherein Y is alkyl, alkenyl, alkynyl, dialkylamino, cyano, alkylsulfonyl, aryl or arysulfonyl groups, said aryl groups being optionally substituted with halogen or alkyl substituents having no more than ten carbon atoms.

34. A composition in accordance with claim 33 wherein A is a three- or four-membered divalent chain which may include one or more sulfur or oxygen atoms; or nitrogen atoms which are optionally substituted with alkyl, alkenyl, alkoxyalkyl or acyl groups containing no more than six aliphatic carbon atoms; or carbon atoms which are optionally substituted with an oxo or dicyanomethylidene moiety; or an imino group which may be substituted with alkyl, or dialkylamino groups containing no more than ten carbon atoms; or one or more alkyl groups containing no more than six carbon atoms.

35. A composition in accordance with claim 33 wherein the active toxicant is O-Ethyl-S-propyl-O-(5,5-dimethyl-2-isopropylimino-1,3-dithiolan-4-ylimino) phosphorothioate.

36. A composition in accordance with claim 33 wherein the active toxicant is O-Ethyl-S-propyl-O-(5,5- dimethyl-2-sec-butylimino-1,3-dithiolan-4-ylimino) phosphorothioate.

37. A composition in accordance with claim 33 wherein the active toxicant is O-Ethyl-S-propyl-O-(5,5-dimethyl-2-tert-butylimino-1,3-dithiolan-4-ylimino) phosphorothioate.

38. A composition in accordance with claim 33 wherein the active toxicant is O-Ethyl-S-propyl-O-(5,5-dimethyl-2-dimethylhydrazono-1,3-dithiolan-4-ylimino) phosphorothioate.

39. A method of controlling insects, mites or nematodes which comprises subjecting them to an insecticidally, miticidally or nematocidally effective amount of a compound of the formula:

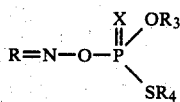

wherein:
X is oxygen or sulfur;
$R_3$ and $R_4$ are individually alkyl; provided that the total number of aliphatic carbon atoms in each of $R_3$ and $R_4$ does not exceed six;
R is:

a. 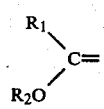

wherein:
$R_1$ is alkyl, cycloalkyl or phenyl, all of which may be unsubstituted or substituted with one or more alkyl, halogen, alkoxy or alkylthio substituents; provided that the total number of aliphatic carbon atoms in any alkyl, alkoxy or alkylthio substituent may not exceed eight; and provided further that the total number of aliphatic carbon atoms in R may not exceed sixteen; and provided further that when $R_1$ is cycloalkyl, the total number of aliphatic carbon atoms in said cycloalkyl ring structure may be no less than three and may not exceed six;
$R_2$ is alkyl, provided that the total number of aliphatic carbon atoms in $R_2$ does not exceed eight; or b. 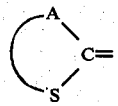

wherein:
A is a three- or four-membered divalent aliphatic chain, which may be optionally substituted by one or more alkyl groups each containing no more than six carbon atoms, and which may include in said chain one or more divalent:
sulfur, sulfinyl, sulfonyl, oxygen, carbonyl, thiono or dicyanomethylidene moieties; or
amino moieties, which may be optionally substituted with with alkyl, alkenyl, alkoxyalkyl or acyl groups having no more than six carbon atoms; or
imino moieties of the formula:

wherein Y is alkyl, alkenyl, alkynyl, dialkylamino, cyano, alkylsulfonyl, aryl or arylsulfonyl groups, said aryl groups being optionally substituted with halogen or alkyl substituents having no more than ten carbon atoms.

40. A method in accordance with claim 39 wherein X is oxygen.

41. A method in accordance with claim 39 wherein X is sulfur.

42. A method in accordance with claim 39 wherein $R_3$ is ethyl and $R_4$ is propyl.

43. A method of controlling insects, mites and nematodes which comprises subjecting them to an insecticidally, miticidally or nematocidally effective amount of a compound of the formula:

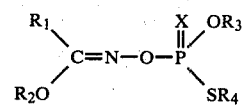

wherein:
X is either oxygen or sulfur;
$R_1$ is alkyl, cycloalkyl or phenyl, all of which may be unsubstituted or substituted with one or more alkyl, halogen, alkoxy or alkylthio substituents; provided that the total number of aliphatic carbon atoms in any alkyl, alkoxy or alkylthio substituent may not exceed eight; and provided further that the total number of aliphatic carbon atoms in $R_1$ may not exceed sixteen; and provided further that when $R_1$ is cycloalkyl, the total number of aliphatic carbon atoms in said cycloalkyl ring structure may be no less than three and may not exceed six;
$R_2$ is alkyl, provided that the total number of aliphatic carbon atoms in $R_2$ does not exceed eight;
$R_3$ and $R_4$ are individually alkyl.

44. A method in accordance with claim 43 wherein the compound is O-Ethyl-S-propyl-O-(1-methoxyethylidenamino)phosphorothioate.

45. A method in accordance with claim 43 wherein the compound is O-Ethyl-S-propyl-O-(1-ethoxyethylidenamino)phosphorothioate.

46. A method in accordance with claim 43 wherein the compound is O-Ethyl-S-propyl-O-(1-ethoxybenzylidenamino)phosphorothioate.

47. A method of controlling insects, mites and nematodes which comprises subjecting them to an insecticidally, miticidally or nematocidally effective amount of a compound of the formula:

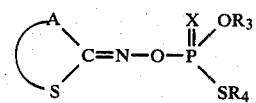

wherein:
X is oxygen or sulfur;
$R_3$ and $R_4$ are individually alkyl;
A is a three- or four-membered divalent aliphatic chain, which may be optionally substituted by one or more alkyl groups each containing no more than six carbon atoms, and which may include in said chain one or more divalent:

sulfur, sulfinyl, sulfonyl, oxygen, carbonyl, thiono or dicyanomethylidene moieties; or amino moieties, which may be optionally substituted with alkyl, alkenyl, alkoxyalkyl or acyl groups having no more than six carbon atoms; or imino moieties of the formula:

wherein Y is alkyl, alkenyl, alkynyl, dialkylamino, cyano, alkylsulfonyl, aryl or arysulfonyl groups, said aryl groups being optionally substituted with halogen or alkyl moieties having no more than ten carbon atoms.

48. A method in accordance with claim 47 wherein A is a three- or four-membered divalent chain which may include one or more sulfur or oxygen atoms; or nitrogen atoms which are optionally substituted with alkyl, alkenyl, alkoxyalkyl, or acyl groups containing no more than six aliphatic carbon atoms; or carbon atoms which are optionally substituted with an oxo or dicyanomethylidene moiety; or an imino group which may be substituted with alkyl, or dialkylamino groups containing no more than ten carbon atoms; or one or more alkyl groups containing no more than six carbon atoms.

49. A method in accordance with claim 47 wherein the compound is O-Ethyl-S-propyl-O-(5,5-dimethyl-2-isopropylimino-1,3-dithiolan-4-ylimino)phosphorothioate.

50. A method in accordance with claim 47 wherein the compound is O-Ethyl-S-propyl-O-(5,5-dimethyl-2-sec-butylimino-1,3-dithiolan-4-ylimino)phosphorothioate.

51. A method in accordance with claim 47 wherein the compound is O-Ethyl-S-propyl-O-(5,5-dimethyl-2-tert-butylimino-1,3-dithiolan-4-ylimino)phosphorothioate.

52. A method in accordance with claim 47 wherein the compound is O-Ethyl-S-propyl-O-(5,5-dimethyl-2-dimethylhydrazono-1,3-dithiolan-4-ylimino)phosphorothioate.

* * * * *